United States Patent
Blumberg et al.

(10) Patent No.: US 12,054,459 B2
(45) Date of Patent: Aug. 6, 2024

(54) PURIFICATION OF BIS-QUATERNARY PYRIDINIUM OXIMES

(71) Applicant: Southwest Research Institute, San Antonio, TX (US)

(72) Inventors: Shawn T. Blumberg, San Antonio, TX (US); Antonio Menchaca, Seguin, TX (US); Christopher Dorsey, San Antonio, TX (US); Asa Waterman, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 356 days.

(21) Appl. No.: 17/649,581

(22) Filed: Feb. 1, 2022

(65) Prior Publication Data

US 2023/0242487 A1 Aug. 3, 2023

(51) Int. Cl.
*C07D 213/81* (2006.01)

(52) U.S. Cl.
CPC ................... *C07D 213/81* (2013.01)

(58) Field of Classification Search
CPC .................................................. C07D 213/81
See application file for complete search history.

(56) References Cited

U.S. PATENT DOCUMENTS 10,633,340 B1 * 4/2020 Blumberg ............ C07D 213/53

OTHER PUBLICATIONS

Rastogi, Journal of Chromatography A, 2001, vol. 933, 91-97. (Year: 2001).*
International Search Report from related PCT application PCT/US2023/060355, dated Jun. 30, 2023.
Petroianu et al., Five oximes (K-27, K48, obidoxime, HI-6 and trimedoxime in comparison with pralidoxime: survival in rats exposed to methyl-paraoxon: J. Appl. Toxicol. 2007, vol. 27: pp. 453-457.
Pang et al., "Rational Design of Alkylene-Linked Bis-Pyridiniumaldoximes as Improved Acetylcholinesterase Reactivators", Chemistry & Biology. 2003, vol. 10: pp. 491-502.
Environmental Protection Agency (EPA). Bis(chloromethyl)ether (BCME), 1992, https://www.epa.gov/sites/production/files/2016-09/documents/bis-chloromethvl-ether.pdf. 5pgs.
Eyer, "The Role of Oximes in the Management of Organophosphorus Pesticide Poisoning", Toxical, Rev. 2003, vol. 22, pp. 165-190.
The National Institute for Occupational Safety and Health (NIOSH), Appendix B—Thirteen OSHA-Regulated Carcinogens, 2016. Center for Disease Control (CDC). https://www.cdc.gov/niosh/npg/nengapdxb.html 1pg.
Van Duuren, Comparison of Potency of Human Carcinogens: Vinyl Chloride, Chloromethylmethyl Ether and Bis (Chloromethyl) Ether, Environ Res., 49 (2), pp. 143-151, 1989.
Wilhelm, "A Comprehensive Evaluation of the Efficacy of Leading Oxime Therapies in Guinea Pigs Exposed to Organophosphorus Chemical Warfare Agents or Pesticides", Toxicology and Applied Pharmacology 281, pp. 254-265, 2014.

* cited by examiner

*Primary Examiner* — D Margaret M Seaman

(74) *Attorney, Agent, or Firm* — Grossman, Tucker, Perreault & Pfleger, PLLC

(57) ABSTRACT

Purification of bis-quaternary pyridinium oximes (BQPO) which may serve as organophosphorus nerve agent antidotes.

30 Claims, No Drawings

PURIFICATION OF BIS-QUATERNARY PYRIDINIUM OXIMES

GOVERNMENT SUPPORT CLAUSE

This invention was made with United States Government Defense Threat Reduction Agency (DTRA) support, under Contract No. 51203, Project No. 26353. The Government has certain rights in this invention.

FIELD

The present invention relates to purification of bis-quaternary pyridinium oximes (BQPO) which may serve as organophosphorus nerve agent antidotes.

BACKGROUND

Stimulating signals are typically carried by acetylcholine within a nervous system synapse. Such signals may be discontinued by a specific type of cholinesterase enzymes, acetylcholinesterase, which breaks down acetylcholine. If cholinesterase inhibiting chemicals are present, they may then prevent the breakdown of acetylcholine thereby disrupting normal nervous system activity. For example, certain chemical classes of pesticides, such as organophosphates and carbamates, may result in toxic cholinesterase inhibition. Accordingly, if an individual is regularly exposed to such inhibitors, there remains a need to prophylactically or therapeutically treat such toxicity. Among other things, individuals or animals who may have been exposed to a carbamate type cholinesterase inhibitor may currently be treated with atropine, and those exposed to organophosphates may beneficially be treated with a pralidoxime antidote.

Organophosphorous nerve agents (OPNA) have been used as chemical weapons, and as noted, in pesticides, have reportedly cause an estimated 300,000 deaths per year worldwide. See, e.g., Eyer, P. et al, *Toxicol. Rev.* 2003, 22, 165-90. Currently, the bis-pyridinium oximes known as: (1) HLö-7 dimethylsulfate (DMS), otherwise known as 1-[[[4-(aminocarbonyl)pyridinio]methoxy]methyl]-2,4-bis[(hydroxyimino)methyl]pyridinium dimethane sulfonate; (2) HI-6 DMS, otherwise known as (1-[[[4-(aminocarbonyl)pyridinio]methoxy]methyl]-2-[(hydroxyimino)methyl]pyridinium dimethane sulfonate); and (3) obidoxime DMS, otherwise known as oxo-[[1-[[4-(oxoazaniumylmethylidene)pyridin-1-yl]methoxymethyl]pyridin-4-ylidene]methyl]azanium dimethane sulfonate, are reportedly among the most effective reactivators of OPNA inhibited acetylcholinesterase (AChE).

However, current methods to synthesize the above referenced antidotes require the use of chemical compounds which are extremely toxic and which lead to relatively large amounts of side products that are difficult to remove from the reaction media.

In U.S. Pat. No. 10,633,340, there is disclosed a method of forming bis-quaternary pyridinium oximes (BQPO) in a relatively less toxic route with relatively higher purity comprising:

supplying benzoic anhydride having the following structure:

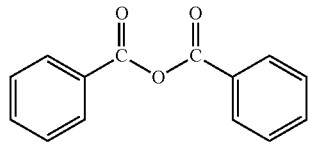 [SMILES: O=C(OC(=O)c1ccccc1)c1ccccc1]

reacting said benzoic anhydride with trioxane to form a dibenzoyloxymethyl ether having the following structure

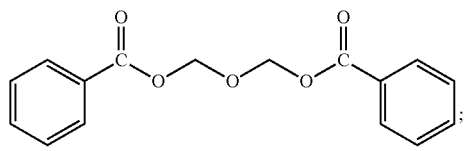 [SMILES: O=C(OCOCOC(=O)c1ccccc1)c1ccccc1]

supplying a substituted pyridine having the following structure:

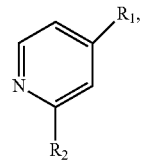

wherein $R_1$ and $R_2$ may be independently selected from the group consisting of hydrogen, alkyl, —CH═NOH or —CONH$_2$;

combining said dibenzyl acetoxymethyl ether with said substituted pyridine and forming a salt having the following structure:

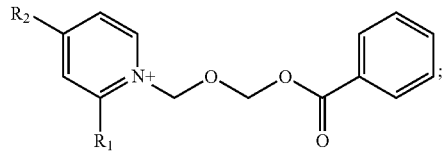

reacting said salt with a substituted pyridine having the following structure:

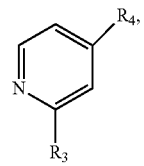

wherein $R_1$ and $R_2$ may be independently selected from the group consisting of hydrogen, alkyl group, —CH═NOH or —CONH$_2$;

and forming the following BPQO structure:

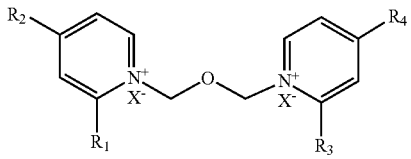

wherein $R_3$ and $R_4$ may be independently selected from the group consisting of hydrogen, alkyl, —CH=NOH or —CONH$_2$ and $X^-$ comprises Cl—, Br—, I— or $^-OSO_2CH_3$.

Accordingly, while bis-quaternary pyridinium oximes have been produced at relatively acceptable reagent quality there remains a need for newer procedures to purify, extract or otherwise manipulate bis-quaternary pyridinium oximes in order to provide, e.g., improved active pharmaceutical ingredient (API) purity.

SUMMARY

A method of improving the relative purity of bis-quaternary pyridinium oximes comprising supplying a bis-quaternary pyridinium oxime of the following structure:

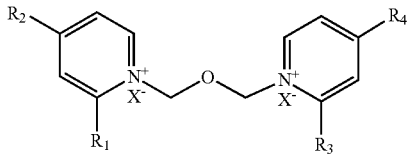

where $R_1$, $R_2$, $R_3$ and $R_4$ may be independently selected from the group consisting of hydrogen, alkyl, —CH=NOH or —CONH$_2$ and $X^-$ comprises Cl$^-$, Br$^-$, I$^-$ or $^-OSO_2CH_3$. This is then followed by treating said bis-quaternary pyridinium oxime with an alkyl phosphate of the formula $Z_2PO4$, where Z is an alkyl group and forming a bis-quaternary pyridinium oxime, of the following structure:

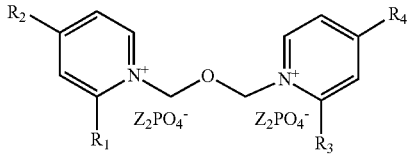

This is the followed by treating said bis-quaternary pyridinium oxime with an acid HY, wherein Y comprises Cl, Br, I or $OSO_2CH_3$ and recovering a bis-quaternary pyridinium oxime of improved relative purity of the following structure:

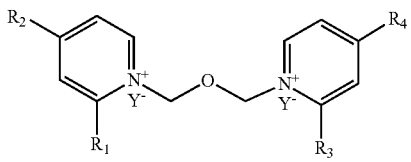

wherein $Y^-$ comprises Cl$^-$, Br$^-$, I$^-$ or $^-OSO_2CH_3$.

A method of improving the relative purity of bis-quaternary pyridinium oximes comprising supplying a bis-quaternary pyridinium oxime of the following structure:

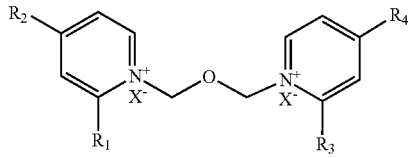

where $R_1$, $R_2$, $R_3$ and $R_4$ may be independently selected from the group consisting of hydrogen, alkyl, —CH=NOH or —CONH$_2$ and $X^-$ comprises Br$^-$, I$^-$ or $^-OSO_2CH_3$. This is then followed by subjecting said bis-quaternary pyridinium oxime to an ion exchange reaction to convert $X^-$ to Cl$^-$ and providing a bis-quaternary pyridinium oxime of the following structure:

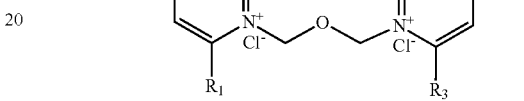

and

This is then followed by placing said bis-quaternary pyridinium oxime in an organic alcohol containing a metal salt and eluting through a chromatography column containing silica as the stationary phase and recovering said bis-quaternary pyridinium oxime produced in step (b) in relatively purified form.

A method of improving the relative purity of bis-quaternary pyridinium oximes comprising supplying a bis-quaternary pyridinium oxime of the following structure:

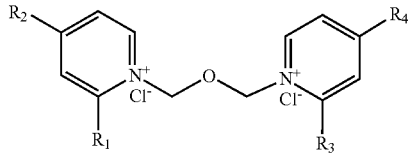

where $R_1$, $R_2$, $R_3$ and $R_4$ may be independently selected from the group consisting of hydrogen, alkyl, —CH=NOH or —CONH$_2$. This is then followed by placing said bis-quaternary pyridinium oxime in an organic alcohol containing a metal salt and eluting through a chromatography column containing silica as the stationery phase and recovering said bis-quaternary pyridinium oxime produced in step (b) in relatively purified form.

DETAILED DESCRIPTION OF PREFERRED EMBODIMENTS

The present invention is directed at improving the relative purity of bis-quaternary pyridinium oximes having the following general structure:

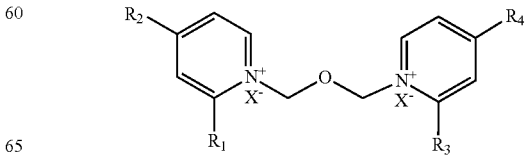

In the above, $R_1$, $R_2$, $R_3$ and $R_4$ may be independently selected from the group consisting of hydrogen, alkyl, —CH=NOH or —CONH$_2$ and X$^-$ comprises Cl$^-$, Br$^-$, I$^-$ or $^-$OSO$_2$CH$_3$. The reference to improved relative purity herein should be understood as improving (e.g., increasing) the relative purity of the starting or supplied bis-quaternary pyridinium oxime, via the purification protocols disclosed herein. Preferred purity levels achieved herein are preferably measured by high pressure liquid chromatography (HPLC). Moreover, the improved purity levels achieved herein can be such that the relatively pure bis-quaternary pyridinium oxime that is recovered may now be particularly suitable for a solvent-based recrystallization purification protocol, so that HPLC purity levels may be raised to even higher comparative levels. Such solvent-based recrystallization protocol can preferably utilize a water/organic alcohol solvent system.

Particular preferred oximes herein for purification herein therefore include: (1) HLö-7 dimethylsulfate (DMS) otherwise known as 1-[[[4-(aminocarbonyl)pyridinio]methoxy]methyl]-2,4-bis[(hydroxyimino)methyl]pyridinium dimethane sulfonate; (2) HI-6 DMS, otherwise known as (1-[[[4-(aminocarbonyl)pyridinio]methoxy]methyl]-2-[(hydroxyimino)methyl]pyridinium dimethane sulfonate); and (3) obidoxime DMS, otherwise known as oxo-[[1-[[4-(oxoazaniumylmethylidene)pyridin-1-yl]methoxymethyl]pyridin-4-ylidene]methyl]azanium dimethane sulfonate; or (4) HLö-7 bischloride.

In a first exemplary embodiment, one therefore supplies compound (1), namely the above referenced relatively impure bis-quaternary pyridinium oximes. Such relatively impure bis-quaternary pyridinium oxime may more specifically indicate an HPLC purity of less than 70.0%. The relatively impure bis-quaternary pyridinium oximes are water soluble, and are then treated and preferably extracted into an organic solvent medium that partitions (separates) with water (e.g. methylene chloride) upon exposure to an alkyl phosphate, of the formula Z$_2$PO$_4$, where Z is an alkyl group. The number of carbons in the alkyl phosphate preferably amounts to at least eight carbon atoms, more preferably at least nine carbon atoms, or even at least ten carbon atoms. A preferred range may therefore be 8-20 carbon atoms. Such carbon atom content provided by Z in Z$_2$PO$_4$ therefore promotes extraction of the water soluble bis-quaternary pyridinium oximes into the organic phase. Preferably the alkyl phosphate comprises bis-(2-ethylhexyl) phosphate (BEHP), C$_{16}$H$_{35}$O$_4$, and the purification proceeds according to the following protocol:

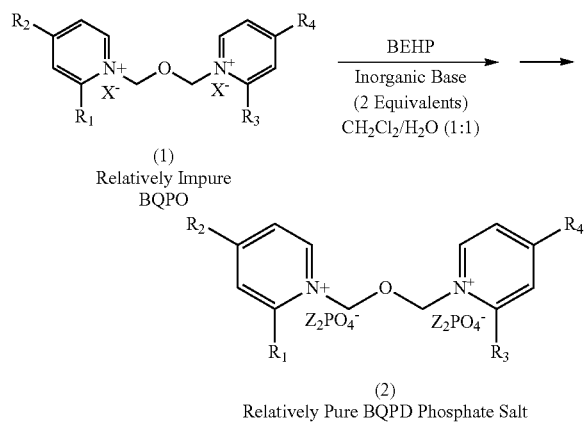

(1)
Relatively Impure
BQPO (2)
Relatively Pure BQPD Phosphate Salt

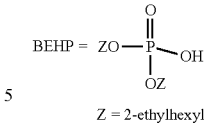

Z = 2-ethylhexyl

In the above, compound (2), the relatively pure bis-quaternary pyridinium oxime that is formed is as illustrated, preferably a salt of bis-(2-ethylhexyl) phosphate. The inorganic base is preferably a sodium or potassium metal salt, such as KHCO$_3$ or NaHCO$_3$. Such inorganic base therefore promotes formation of the alkyl phosphate into ionized form (e.g., Z$_2$PO4$^-$).

Compound (2) may therefore be understood as a bis-quaternary pyridinium oxime phosphate (anion) salt which preferably has a relative purity that is greater than the purity of compound (1). More preferably, the purity of compound (2) as measured by HPLC is such that it has a purity of 70.0% or greater. For example, it preferably indicates a purity in the range of 70.0% to 90.0% as measured by HPLC. In addition, the yield of compound (2), the relative pure bis-quaternary pyridinium oxime phosphate (anion) salt, is greater than or equal to 90.0%, more preferably, 91.0%, 92.0%, 93.0%, 94.0%, 95.0%, 96.0%, 97.0%, 98.0%, 99.0% or 100%, or in the range of 90.0% to 100%.

In the ensuing step of the above referenced purification protocol, compound (2), the relatively pure bis-quaternary pyridinium oxime phosphate (anion) salt, is treated with an acid HY where Y may preferably be a halogen (Cl, Br or I,) as well as a mesylate (OSO$_2$CH$_3$), and Y$^-$ is the corresponding anionic moiety ($^-$Cl, $^-$Br, $^-$I or $^-$OSO$_2$CH$_3$) resulting in the formation and recovery of compound (3), a bis-quaternary pyridinium oxime, as outlined below:

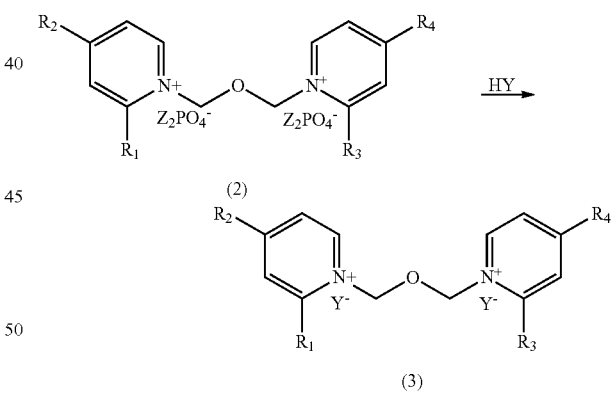

Consistent with the above, the relative purity of isolated compound (3) is preferably 70.0% or greater, and more preferably in the range of 70.0% to 90.0%, as measured by HPLC. Moreover, compound (3) is then particularly suitable for an additional purification protocol, such as solvent recrystallization. Solvent recrystallization of compound (3) can then preferably increase the HPLC purity to levels of greater than 90.0%, such as a HPLC purity level of 91.0%, 92.0%, 93.0%, 94.0%, 95.0%, 96.0%, 97.0%, 98.0%, 99.0% or 100%, or a purity in the range of greater than 90% to 100%, or 95.0% to 100%. In addition, the overall yield of compound (3), from compound (1), is in the range of greater than or equal to 80.0%, e.g., in the range 80.0% to 100%.

Another exemplary protocol for purification of bis-quaternary pyridinium oxime again begins with compound (1), the relatively impure bis-quaternary pyridinium oxime:

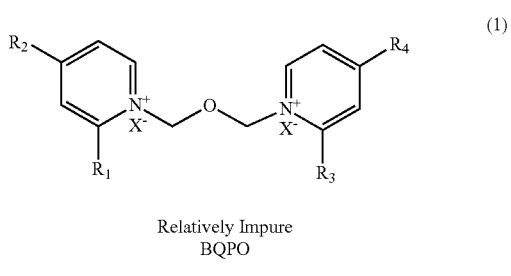

(1)
Relatively Impure
BQPO

If X⁻ is not a Cl⁻ functionality, such as Br⁻, I⁻ or ⁻OSO₂CH₃, one initially and preferably undergoes an ion-exchange reaction to convert X⁻ to Cl⁻ according to the procedure below:

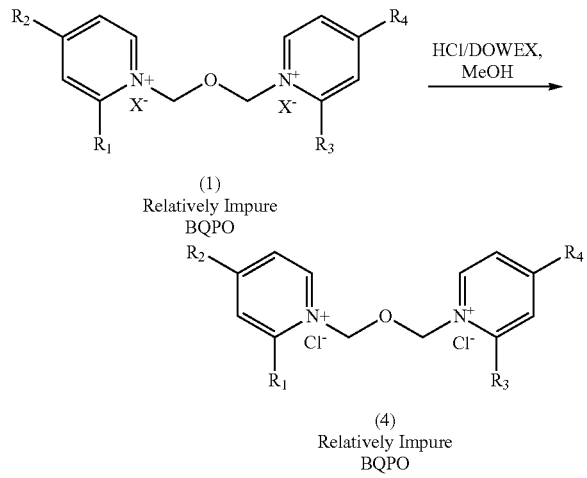

(1)
Relatively Impure
BQPO (4)
Relatively Impure
BQPO

In the above, reference to DOWEX is reference to an ion-exchange resin available from Dow which is a polymer resin that provides the ability to exchanging ions in a solution that is passed through them. In the above, the solution of compound (1) is therefore passed through the ion-exchange resin in the presence of HCl in a methanol (MeOH) medium to provide compound (4), the relatively impure bis-quaternary pyridinium oxime, now in chlorine salt form. Reference again to a relatively impure bis-quaternary pyridinium oxime in chlorine salt form can be understood as a HPLC purity of less than 70.0%.

This is then followed by preparative column chromatography purification. More specifically, preparative column chromatography separation utilizing an organic alcohol solvent (e.g. methanol, ethanol, isopropanol, tert-butanol) containing a metal salt (e.g. CaCl₂, NaBr or NaI). In other words, the bis-quaternary pyridinium oxime in chlorine salt form is placed in an organic alcohol solvent preferably containing CaCl₂ and eluted through a chromatography column that preferably contains silica as the stationary phase. Preferably, the eluting solvent contains the above referenced organic alcohol solvent and the above referenced metal salt, where the metal salt is present at a concentration range of 0.1M to 0.5M, or 0.1M to 0.3M, or 0.2M. Most preferably, the eluting solvent is therefore a 0.2 M CaCl₂ in ethanol, which may then be followed by ethanol on its own, which was observed to provide a purified bis-quaternary pyridinium oximes (chlorine salt) according to the following protocol:

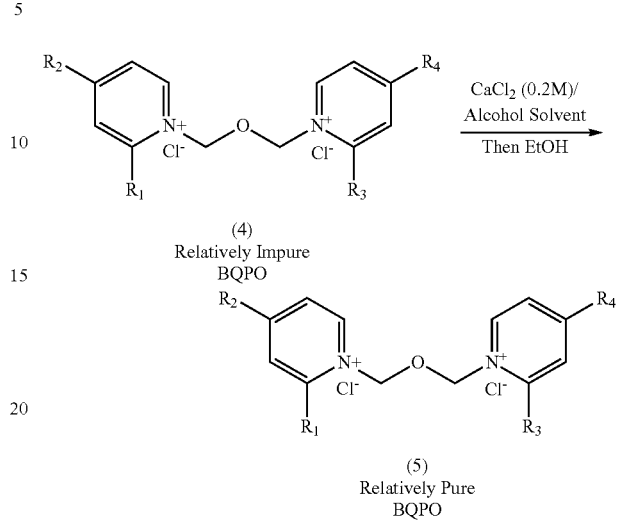

(4)
Relatively Impure
BQPO (5)
Relatively Pure
BQPO

In the above, compound (4), the relatively impure BQPO is converted to compound (5), a relatively pure BQPO. This may be preferably understood as indicating that the HPLC purity level of compound (5) is greater (e.g., higher) than that of compound (4). More preferably, the HPLC purity level of compound (4) is as noted, less than 70.0%, and the HPLC purity of compound (5) is greater than 70.0%, more preferably in the range of 70.0% to 90.0%. In addition, compound (5) may again be subject to a further purification protocol, such as solvent-based recrystallization, where the HPLC purity level of compound (5) is elevated to greater than 90.0%, such as a HPLC purity level of 91.0%, 92.0%, 93.0%, 94.0%, 95.0%, 96.0%, 97.0%, 98.0%, 99.0% or 100%, or a HPLC purity in the range of greater than 90% to 100%, or 95.0% to 100% In addition, the overall yield of compound (5) is in the range of 50.0% to 80.0%, from compound (1).

Working Examples: Ion Pair Extraction

HLö-7 bischloride. Trifluoromethanesulfonate (12.08 g, 9.86 mL, 54.5 mmol) was added to flask containing dibenzoyloxymethyl ether (2.57 g, 6 mmol), pyridine-2,4-dialdoxime (1.00 g, 6 mmol), 2,6-di-tert-butylpyridine (8.43 g, 9.52 mL, 42.4 mmol), and nitromethane (6 mL) that had been purged of oxygen and water by pulling vacuum and refilling with nitrogen three times. The mixture was stirred at 40° C. for 1.5 h. Isonicotinamide (0.739 g, 6 mmol) was then added to the mixture and stirred at 60° C. for 16 h. After that time, the reaction was poured into water (50 mL) and dichloromethane (50 mL) and stirred for 10 minutes. After that time, the layers were separated. 50 mL of fresh dichloromethane was added back to the flask containing the aqueous layer, and the pH of the aqueous layer was adjusted to pH 7 with trioctylamine (~4 mL). After stirring for 5 minutes, the layers were separated. 50 mL of fresh dichloromethane was again added back to the flask containing the aqueous layer along with bis(2-ethylhexyl)phosphate. After stirring for 1 minute, potassium bicarbonate (1.2 g) was added to the mixture, and it was stirred for 10 minutes. After that time, the layers were separated. To the organic layer was added a solution of acetyl chloride (0.86 mL) in methanol (10 mL) producing copious amounts of light brown/tan solid. The suspension was filtered to yield HLö-7 bischloride (1.67 g, 68% yield). HPLC analysis showed it was 85% pure.

Working Examples: Column Chromatography 1

The relatively impure HLö7 (~65 g) was dissolved in MeOH (~100 mL) and concentrated onto silica (~111 g) until it was a free-flowing powder. The solids were transferred to four 60 mL cartridges and purified via column chromatography (4×SiliaSep 220 g, MeOH/0.2 M aq $CaCl_2$ (9:1), isocratic) The purity of each fraction was determined by thin layer chromatography (MeOH/0.2 M aq $CaCl_2$ (3:1)). The desired fractions were collected and concentrated to an oily solid and the material was co-stripped with EtOH (3×100 mL) to isolate a tan solid. EtOH (~100 mL) was added to the solids and stirred at room temperature. The remaining solids were filtered to obtain ~30 g HLö7·2Cl having a HPLC purity of about 85.0%. The mother liquors were concentrated under reduced pressure and EtOH (50 mL) was added. Solids began to crystalize and these solids were filtered to obtain 7-10 g of $Ca(OMs)_2$. The mother liquors were again concentrated under reduced pressure and EtOH (25 mL) was added. Solids began to crystalize and these solids were filtered to obtain 5-6 g of $Ca(OMs)_2$ and Hlo7 DMS (~1:1 by 1H-NMR).

Working Examples: Column Chromatography 2

Relatively impure HLö7 (~15.5 g, mixed counter-ions) was dissolved in MeOH (~100 mL) and filtered through ion exchange resin (310 g, chloride) and the column was washed with MeOH (3×300 mL). The combined filtrates were combined and concentrated onto silica (~20 g) until it was a free-flowing powder. The relatively impure HLö7·2ClH was purified via column chromatography (SiliaSep 25 g, (0→40% 0.2 M aq $CaCl_2$ in IPA). The purity of each fraction was determined by thin layer chromatography (40% 0.2 M aq $CaCl_2$ in IPA) and the desired fractions were collected and concentrated to an oily solid. The crude residue was co-stripped with acetone (3-5×100 mL) before adding EtOH (~50 mL) and stirring the mixture at room temperature for one to two hours. The remaining solids were filtered to obtain 8.06 g HLö7·2Cl that was deemed to be ~85% pure by HPLC.

As may therefore be appreciated, the present invention provides for the ability to provide bis-quaternary pyridinium oximes at relatively improved purity levels. In that regard, it is contemplated that the bis-quaternary pyridinium oximes herein can be purified to a level that is now particularly suitable for incorporation into a pharmaceutical composition as an active pharmaceutical ingredient (API). It is contemplated that the bis-quaternary pyridinium oximes provided herein may be used directly as an API, as they may be further purified by, e.g., recrystallization protocols to preferably achieve a purity level of greater than or equal to 95.0%, which may be necessary for designation as an active pharmaceutical ingredient.

The pharmaceutical composition produced herein from the purified bis-quaternary pyridinium oximes may therefore include oral drugs or parental formulations. An API herein may be understood as an ingredient that is part of a drug that produces intended effects. Accordingly, a pharmaceutical composition herein containing the bis-quaternary pyridinium oximes produced herein, preferably at a purity level of equal to or greater than 95.0%, may be particularly effective reactivators of organophosphorus nerve agent inhibited acetylcholinesterase. The purified bis-quaternary pyridinium oximes may therefore be combined with various excipients (substances included in a pharmaceutical dosage that do not provide therapeutic action but to assist in manufacturing, stability, bioavailability or patient acceptability). Examples of excipients therefore include silica, talc, magnesium carbonate, polyethylene glycol, magnesium stearate, stearic acids and its derivatives, sucrose, saccharine, aspartame, sorbitol, gelatin, cellulose, polyvinylpyrrolidone, and starch.

The foregoing description of various methods and preferred embodiments have been presented for illustration. It is not intended to be exhaustive or to limit the claims to any of the preferred steps disclosed and various modifications remain possible.

The invention claimed is:

1. A method of improving the relative purity of bis-quaternary pyridinium oximes comprising:
   (a) supplying a bis-quaternary pyridinium oxime of the following structure:

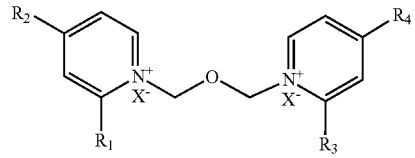

where $R_1$, $R_2$, $R_3$ and $R_4$ may be independently selected from the group consisting of hydrogen, alkyl, —CH=NOH or —$CONH_2$ and $X^-$ comprises $Cl^-$, $Br^-$, $I^-$ or $^-OSO_2CH_3$;

(b) treating said bis-quaternary pyridinium oxime with an alkyl phosphate of the formula $Z_2PO4$, where Z is an alkyl group and forming a bis-quaternary pyridinium oxime, of the following structure:

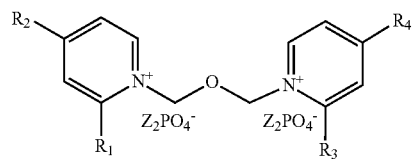

(c) treating said bis-quaternary pyridinium oxime with an acid HY, wherein Y comprises Cl, Br, I or $OSO_2CH_3$;
   (d) recovering a bis-quaternary pyridinium oxime of improved relative purity of the following structure:

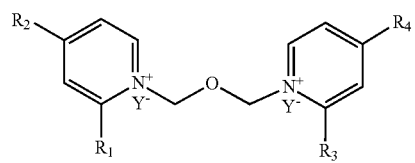

wherein $Y^-$ comprises $Cl^-$, $Br^-$, $I^-$ or $^-OSO_2CH_3$.

2. The method of claim 1 wherein said bis-quaternary pyridinium oxime comprises HLö-7 dimethylsulfate.

3. The method of claim 1 wherein said bis-quaternary pyridinium oxime comprises HI-6 dimethylsulfate.

4. The method of claim 1 wherein said bis-quaternary pyridinium oxime comprises obidoxime dimethylsulfate.

5. The method of claim 1 wherein said bis-quaternary pyridinium oxime comprises HLö-7 bischloride.

6. The method of claim 1 wherein the number of carbon atoms in the alky phosphate is at least eight carbon atoms.

7. The method of claim 1 wherein said alkyl phosphate comprises bis-(2-ethylhexyl) phosphate.

8. The method of claim 1 wherein said bis-quaternary pyridinium oxime salt recovered in step (d) is recovered at a yield of greater than or equal to 80.0%.

9. The method of claim 1 wherein said bis-quaternary pyridinium oxime introduced in step (a) indicates a HPLC purity of less than 70.0%.

10. The method of claim 1 wherein said bis-quaternary pyridinium oxime recovered in step (d) indicates a HPLC purity of greater than 70.0%.

11. The method of claim 1 wherein said bis-quaternary pyridinium oxime recovered in step (d) undergoes solvent recrystallization and indicates a HPLC purity of greater than 90.0%.

12. The method of claim 11 wherein said bis-quaternary pyridinium oxime salt with a HPLC purity of greater than 90.0% is combined with one or more excipients and forming a pharmaceutical composition.

13. A method of improving the relative purity of bis-quaternary pyridinium oximes comprising:
  a. supplying a bis-quaternary pyridinium oxime of the following structure:

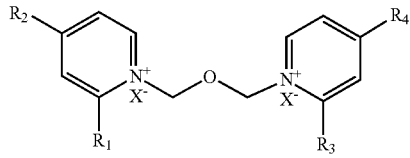

where $R_1$, $R_2$, $R_3$ and $R_4$ may be independently selected from the group consisting of hydrogen, alkyl, —CH=NOH or —CONH$_2$ and X$^-$ comprises Br$^-$, I$^-$ or $^-$OSO$_2$CH$_3$;
  b. subjecting said bis-quaternary pyridinium oxime to an ion exchange reaction to convert X$^-$ to Cl$^-$ and providing a bis-quaternary pyridinium oxime of the following structure:

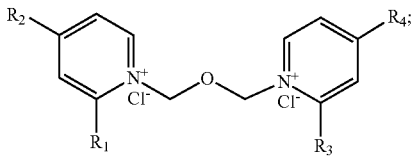

and
  c. placing said bis-quaternary pyridinium oxime in an organic alcohol containing a metal salt and eluting through a chromatography column containing silica as the stationery phase and recovering said bis-quaternary pyridinium oxime produced in step (b) in relatively purified form.

14. The method of claim 13 wherein said organic alcohol in step (c) comprises methanol, ethanol, isopropanol, or tert-butanol.

15. The method of claim 13 wherein said metal salt in step (c) comprises calcium chloride sodium bromide or sodium iodide.

16. The method of claim 13 wherein said calcium chloride, sodium bromide, or sodium iodide is present at a concentration of 0.1 M to 0.5 M.

17. The method of claim 13 wherein said metal salt in step (c) comprises calcium chloride at 0.1M to 0.3M.

18. The method of claim 13 wherein said bis-quaternary pyridinium oxime introduced in step (a) indicates a HPLC purity of less than 70.0%.

19. The method of claim 13 wherein said bis-quaternary pyridinium oxime recovered in step (c) indicates a HPLC purity of greater than 70.0%.

20. The method of claim 13 wherein said bis-quaternary pyridinium oxime recovered in step (c) undergoes solvent recrystallization and indicates a HPLC purity of greater than 90.0%.

21. The method of claim 20 wherein said purified bis-quaternary pyridinium oxime salt with a HPLC purity of greater than 90.0% is combined with one or more excipients and forming a pharmaceutical composition.

22. A method of improving the relative purity of bis-quaternary pyridinium oximes comprising:
  a. supplying a bis-quaternary pyridinium oxime of the following structure:

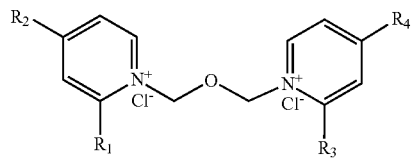

where $R_1$, $R_2$, $R_3$ and $R_4$ may be independently selected from the group consisting of hydrogen, alkyl, —CH=NOH or —CONH$_2$;
  b. placing said bis-quaternary pyridinium oxime in an organic alcohol containing a metal salt and eluting through a chromatography column containing silica as the stationery phase and recovering said bis-quaternary pyridinium oxime produced in step (b) in relatively purified form.

23. The method of claim 22 wherein said organic alcohol in step (b) comprises methanol, ethanol, isopropanol or tert-butanol.

24. The method of claim 22 wherein said metal salt in step (b) comprises calcium chloride sodium bromide or sodium iodide.

25. The method of claim 22 wherein said calcium chloride, sodium bromide, or sodium iodide is present at a concentration of 0.1 M to 0.5 M.

26. The method of claim 22 wherein said metal salt in step (c) comprises calcium chloride at 0.1M to 0.3M.

27. The method of claim 22 wherein said bis-quaternary pyridinium oxime introduced in step (a) indicates a HPLC purity of less than 70.0%.

28. The method of claim 22 wherein said bis-quaternary pyridinium oxime recovered in step (b) indicates a HPLC purity of greater than 70.0%.

29. The method of claim 22 wherein said bis-quaternary pyridinium oxime recovered in step (b) undergoes solvent recrystallization and indicates a HPLC purity of greater than 90.0%.

30. The method of claim 29 wherein said bis-quaternary pyridinium oxime salt with a HPLC purity of greater than 90.0% is combined with one or more excipients and forming a pharmaceutical composition.

* * * * *